US012653594B2

(12) United States Patent
Ricciardi et al.

(10) Patent No.: US 12,653,594 B2
(45) Date of Patent: Jun. 16, 2026

(54) REDUCTION CLAMP FOR LAPIDUS FUSION

(71) Applicant: Arthrex, Inc., Naples, FL (US)

(72) Inventors: Giovanni Ricciardi, Munich (DE);
Alyssa Morgan, Naples, FL (US);
Chris Powell, Naples, FL (US);
Gabriel Cardenas, House Springs, MO
(US); Ryan Rigby, Wellsvillle, UT
(US)

(73) Assignee: Arthrex, Inc., Naples, FL (US)

( * ) Notice: Subject to any disclaimer, the term of this
patent is extended or adjusted under 35
U.S.C. 154(b) by 0 days.

(21) Appl. No.: 18/815,965

(22) Filed: Aug. 27, 2024

(65) Prior Publication Data

US 2025/0072936 A1     Mar. 6, 2025

Related U.S. Application Data

(60) Provisional application No. 63/579,079, filed on Aug.
28, 2023.

(51) Int. Cl.
| | |
|---|---|
| *A61B 17/88* | (2006.01) |
| *A61B 17/17* | (2006.01) |
| *A61B 17/28* | (2006.01) |
| *A61B 17/29* | (2006.01) |
| *A61B 17/56* | (2006.01) |

(52) U.S. Cl.
CPC ...... *A61B 17/8866* (2013.01); *A61B 17/1775*
(2016.11); *A61B 17/2812* (2013.01); *A61B
17/56* (2013.01); *A61B 2017/293* (2013.01);
*A61B 2017/565* (2013.01)

(58) Field of Classification Search
CPC . A61B 17/1775; A61B 17/02; A61B 17/2812;
A61B 2017/2908; A61B 2017/2929;
A61B 2017/293; A61B 2017/565; A61B
17/848; A61B 17/8866
See application file for complete search history.

(56) References Cited

U.S. PATENT DOCUMENTS

| | | | | |
|---|---|---|---|---|
| 7,473,222 | B2 * | 1/2009 | Dewey | A61B 17/3439 |
| | | | | 600/233 |
| 7,507,242 | B2 * | 3/2009 | Triplett | A61B 90/94 |
| | | | | 606/87 |
| 8,162,996 | B2 | 4/2012 | Schelling | |
| 9,339,319 | B2 * | 5/2016 | Schmuck | A61B 17/2804 |
| 10,342,590 | B2 | 7/2019 | Bays | |
| 2012/0303067 | A1 * | 11/2012 | Van Citters | A61B 17/8866 |
| | | | | 606/281 |
| 2021/0361330 | A1 | 11/2021 | Mcaleer | |
| 2022/0361930 | A1 * | 11/2022 | Chan | A61B 17/2804 |
| 2022/0395308 | A1 | 12/2022 | Awtrey | |
| 2023/0048763 | A1 * | 2/2023 | Woodard | A61B 17/2804 |

FOREIGN PATENT DOCUMENTS

WO          2021222216 A1     11/2021

OTHER PUBLICATIONS

US 11,439,381 B2, 09/2022, Jason (withdrawn)

* cited by examiner

*Primary Examiner* — Larry E Waggle, Jr.
(74) *Attorney, Agent, or Firm* — McDonnell Boehnen
Hulbert & Berghoff LLP

(57)          ABSTRACT
The present disclosure provides a device for use in a Lapidus
fusion procedure and methods of use.

11 Claims, 4 Drawing Sheets

100

REDUCTION CLAMP FOR LAPIDUS FUSION

CROSS-REFERENCE TO RELATED APPLICATIONS

This application claims priority to U.S. Provisional Application No. 63/579,079 entitled "Reduction Clamp for Lapidus Fusion," filed on Aug. 28, 2023, the contents of which are hereby incorporated by reference in its entirety.

BACKGROUND

Hallux valgus, more commonly known as bunions, is a condition where the first metatarsal deviates away from the second metatarsal. This results in an intermetatarsal angle that is too large. Bunions are caused when certain tendons, ligaments, and supportive structures of the first metatarsal no longer function correctly causing the first metatarsal to be misaligned. Bunions may be caused by a variety of conditions intrinsic to the structure of the foot, such as flat feet, excessive ligamentous flexibility, abnormal bone structure, and certain neurological conditions.

Bunions are commonly associated with arthritis of the first metatarsal, diminished and/or altered range of motion and discomfort when pressure is applied to the first metatarsal or with motion of the joint. Treatments of bunions vary and, depending on severity of the misalignment, can range from rest, medication, orthotics and, in extreme cases, surgery. Once such surgery is Lapidus fusion, which involves fusing the joint between the first metatarsal bone and one of the small bones in the midfoot called the medial cuneiform. Surgery includes removing the cartilage surfaces from both bones, correcting the angular deformity, then placing hardware (screws and often a small plate) to allow the two bones to grow together, or fuse. In such procedures, changes to the intermetatarsal angle and the pronation of the first metatarsal may be needed prior to fusion.

The present disclosure provides an improved device for use in such Lapidus fusion procedures.

SUMMARY

The disclosure herein includes a reduction clamp for Lapidus fusion and methods of use.

In particular, in one aspect, the present disclosure includes a device comprising a first rod having a first end and a second end opposite the first end. The device also includes a second rod having a first end and a second end opposite the first end. The first rod is rotatably coupled to the second rod between the first end of the second rod and the second end of the second rod. A movement of the second end of the first rod towards the second end of the second rod causes a distance between the first end of the first rod and the first end of the second rod to increase. The device also includes a first locking mechanism configured to fix the distance between the first end of the first rod and the first end of the second rod. The device also includes a joint positioned between a first portion of the second rod including the first end and a second portion of the second rod including the second end. The joint enables a rotation of the first portion of the second rod with respect to the second portion of the second rod about a longitudinal axis of the first portion of the second rod. The device also includes a second locking mechanism configured to fix the rotation of the first portion of the second rod with respect to the second portion of the second rod.

These as well as other aspects, advantages, and alternatives, will become apparent to those of ordinary skill in the art by reading the following detailed description, with reference where appropriate to the accompanying drawings.

DETAILED DESCRIPTION

Figure 1:
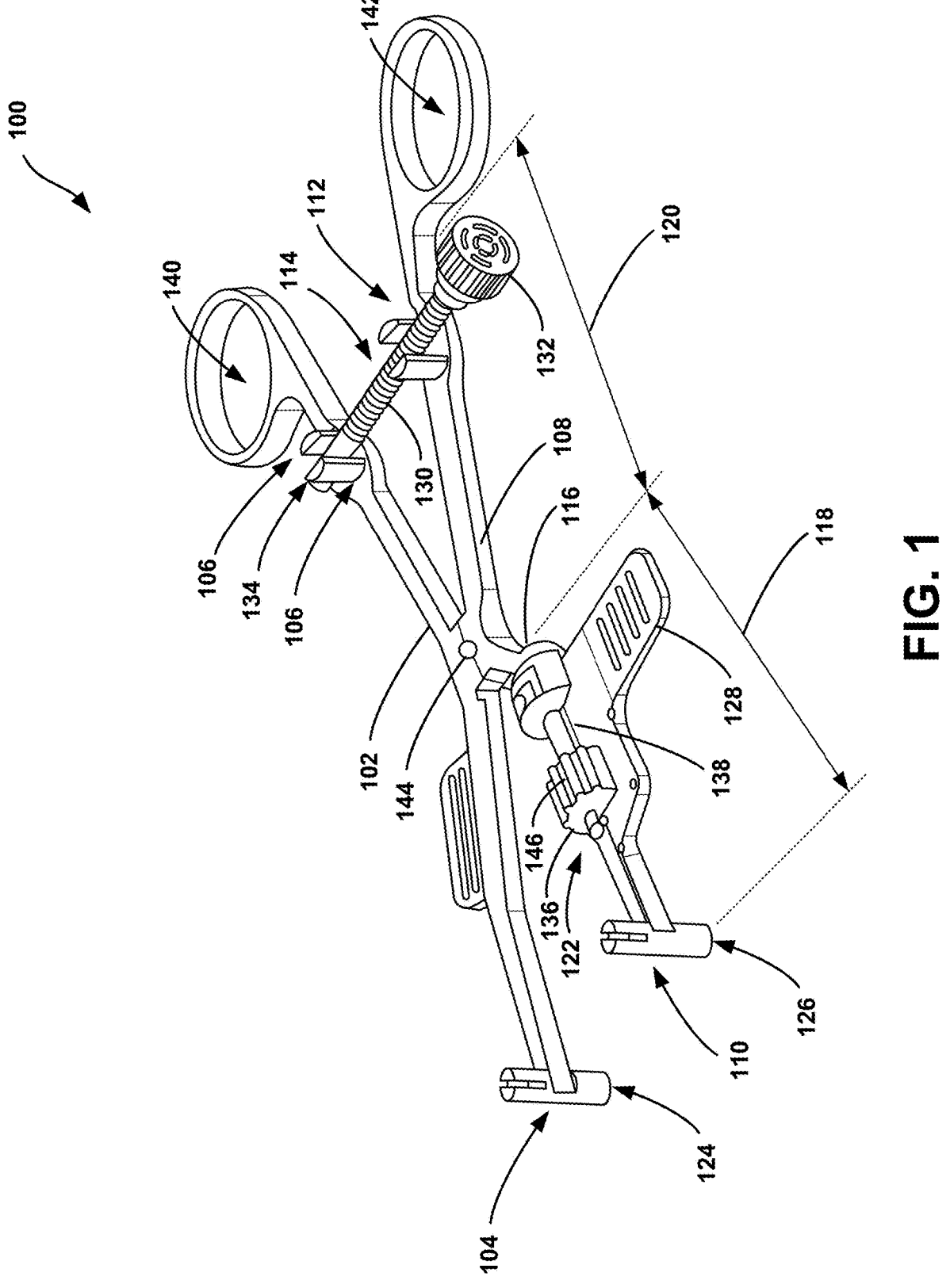
FIG. 1 is a perspective view of an example device for use in a Lapidus fusion procedure.

With reference to the Figures, FIGS. 1-4 illustrate a device 100 for use in a Lapidus fusion procedure. As shown in FIGS. 1-4, the device 100 includes a first rod 102 having a first end 104 and a second end 106 opposite the first end 104. The device 100 also includes a second rod 108 having a first end 110 and a second end 112 opposite the first end 110. The first rod 102 is rotatably coupled to the second rod 108 between the first end 110 of the second rod 108 and the second end 112 of the second rod 108. In use, the first rod 102 and the second rod 108 are configured to move with respect to one another in a plane. A movement of the second end 106 of the first rod 102 towards the second end 112 of the second rod 108 causes a distance between the first end 104 of the first rod 102 and the first end 110 of the second rod 108 to increase. Conversely, movement of the second end 106 of the first rod 102 away from the second end 112 of the second rod 108 causes the distance between the first end 104 of the first rod 102 and the first end 110 of the second rod 108 to decrease.

The device 100 also includes a first locking mechanism 114 configured to fix the distance between the first end 104 of the first rod 102 and the first end 110 of the second rod 108. The device 100 also includes a joint 116 positioned between a first portion 118 of the second rod 108 including the first end 110 and a second portion 120 of the second rod 108 including the second end 112. The joint 116 enables a rotation of the first portion 118 of the second rod 108 with respect to the second portion 120 of the second rod 108 about a longitudinal axis of the first portion 118 of the second rod 108. The device 100 also includes a second locking mechanism 122 configured to fix the rotation of the first portion 118 of the second rod 108 with respect to the second portion 120 of the second rod 108.

In an example, the first end 104 of the first rod 102 includes a first through-hole 124 configured to receive a first K-wire 148, and the first end 110 of the second rod 108 includes a second through-hole 126 configured to receive a second K-wire 150. In one such example, the first through-hole 124 and the second through-hole 126 each include a gripping mechanism configured to prevent the first K-wire 148 and the second K-wire 150 from slipping. The gripping mechanism may comprise an elastic material positioned within the first through-hole 124 and the second through-hole 126, as a non-limiting example.

In an example, the device 100 further includes a handle 128 coupled to the first portion 118 of the second rod 108. A rotation of the handle 128 corresponds to the rotation of the first portion 118 of the second rod 108 with respect to the second portion 120 of the second rod 108 about the longitudinal axis of the first portion 118 of the second rod 108. In one example, as shown in FIGS. 1-4, the handle 128 comprises a tab with a plurality of ridges.

Figure 4:
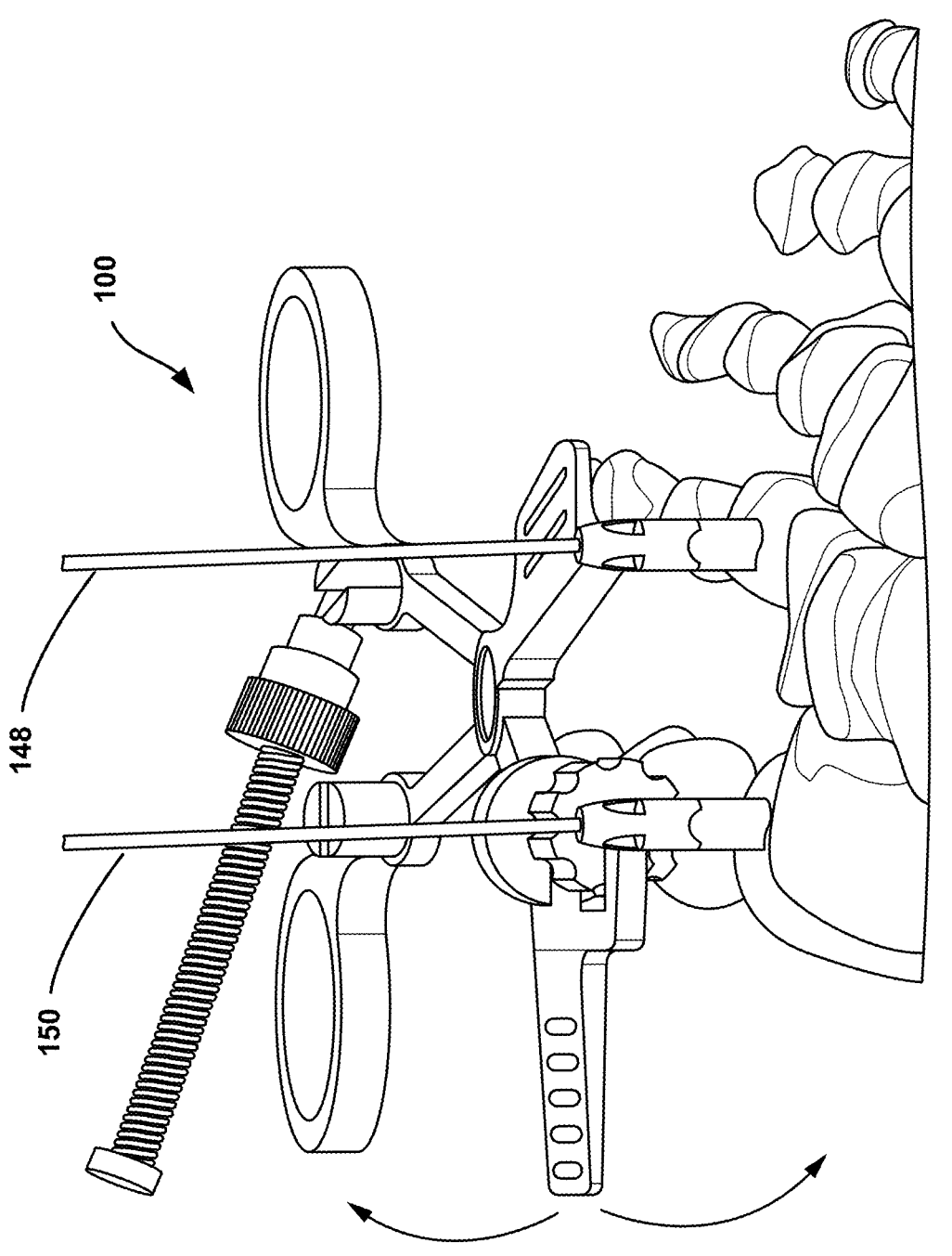
FIG. 4 illustrates a first metatarsal pronation correction using the example device of FIG. 1.

In an example, the first locking mechanism 114 comprises a threaded rod 130 coupled to at least one of the first rod 102 and the second rod 108. In one example, the threaded rod 130 is positioned adjacent the second end 106 of the first rod 102 and the second end 112 of the second rod 108. The device 100 may further include a knob 132 positioned on the threaded rod 130. In one example, the threaded rod 130 is coupled to one of the first rod 102 or the second rod 108 via a joint 134. In such an example, the threaded rod 130 is able to swing around the joint 134 so that it can either be connected to both the first rod 102 and the second rod 108 (as shown in FIG. 1), or only coupled to one of the first rod 102 or the second rod 108 (as shown in FIG. 4).

When the threaded rod 130 is coupled to both the first rod 102 and the second rod 108, a rotation of the knob 132 in a clock-wise direction causes the knob 132 to move in the direction of the axis of the threaded rod 130 and press onto the second end 112 of the second rod 108 causing the distance between the first end 104 of the first rod 102 and first end 110 of the second rod 108 to increase. As such, by turning the knob 132 in a clock-wise direction when the threaded rod 130 is engaged into the first rod 102, the intermetatarsal angle is increased. Since the knob 132 can only move in the direction of the threaded rod 130 when it is turned, the knob 132 also acts as a stopper by holding the intermetatarsal angle adjustment to thereby fix the distance between the first end 104 of the first rod 102 and the first end 110 of the second rod 108.

In an example, the second locking mechanism 122 comprises a knob 136 including a plurality of grooves 146. In a first position, a protrusion 138 of a handle 128 coupled to the first portion 118 of the second rod 108 does not contact the plurality of grooves 146 such that the first portion 118 of the second rod 108 is freely rotatable with respect to the second portion 120 of the second rod 108. In a second position, the protrusion 138 of the handle 128 contacts one of the plurality of grooves such that the first portion 118 of the second rod 108 is rotatably fixed with respect to the second portion 120 of the second rod 108.

In an example, the second end 106 of the first rod 102 includes a first through-hole 140 configured to receive a finger of a surgeon, and the second end 112 of the second rod 108 includes a second through-hole 142 configured to receive a second finger of the surgeon.

In an example, the first rod 102 is rotatably coupled to the second rod 108 via a pin 144. As such, the device 100 may utilize a scissor mechanism to move the second end 106 of the first rod 102 closer and further away from the second end 112 of the second rod 108 to thereby close the intermetatarsal angle.

Figure 3:
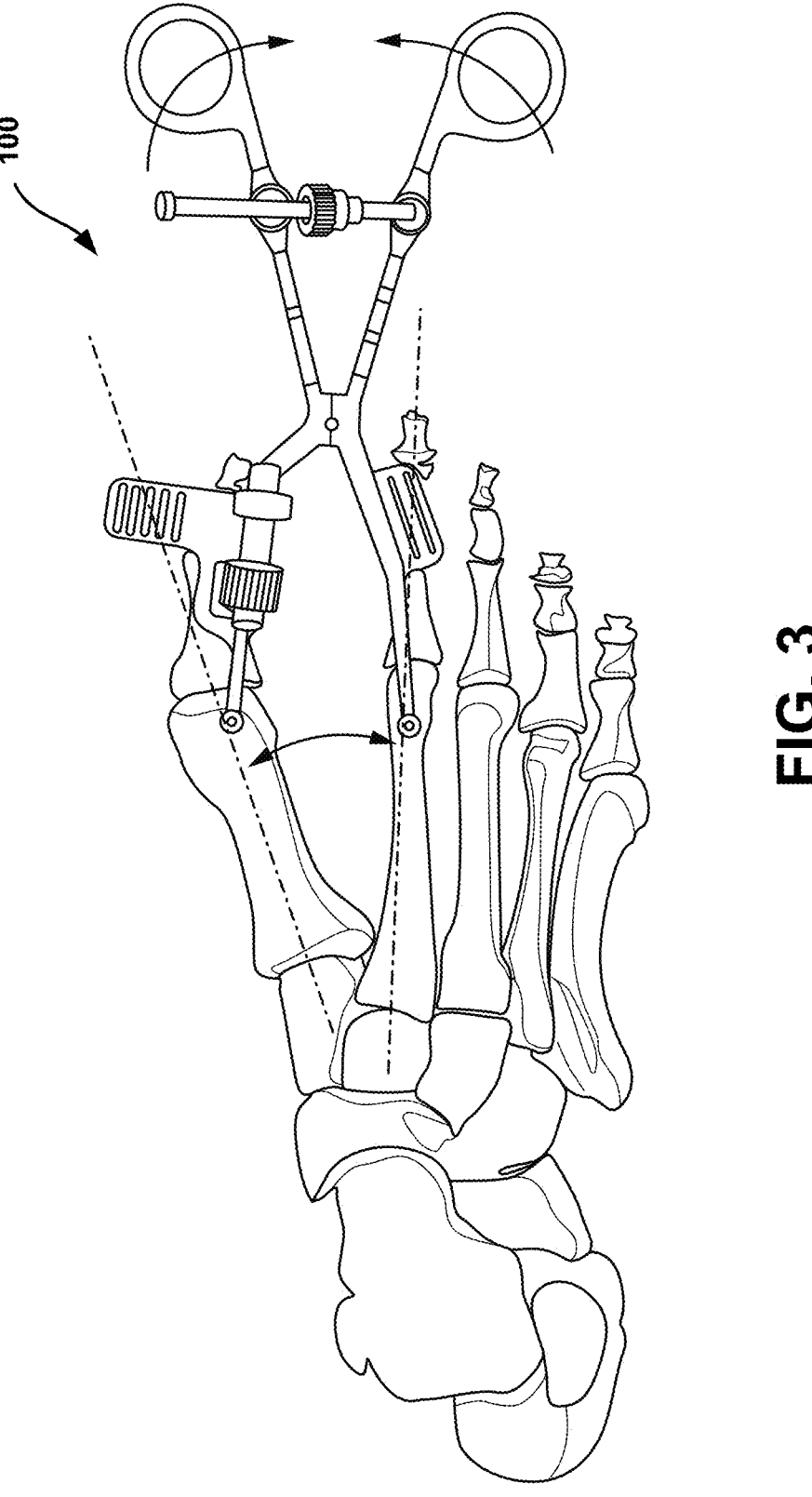
FIG. 3 illustrates an intermetatarsal angle correction using the example device of FIG. 1.

In use, the device 100 is intended to correct hallux valgus deformities and to hold the correction while preparing the first metatarsal joint for fusion using the Lapidus approach. By means of this device 100, both the intermetatarsal angle as shown in FIG. 3 and the pronation of the first metatarsal as shown in FIG. 4 can be corrected independently.

Figure 2:
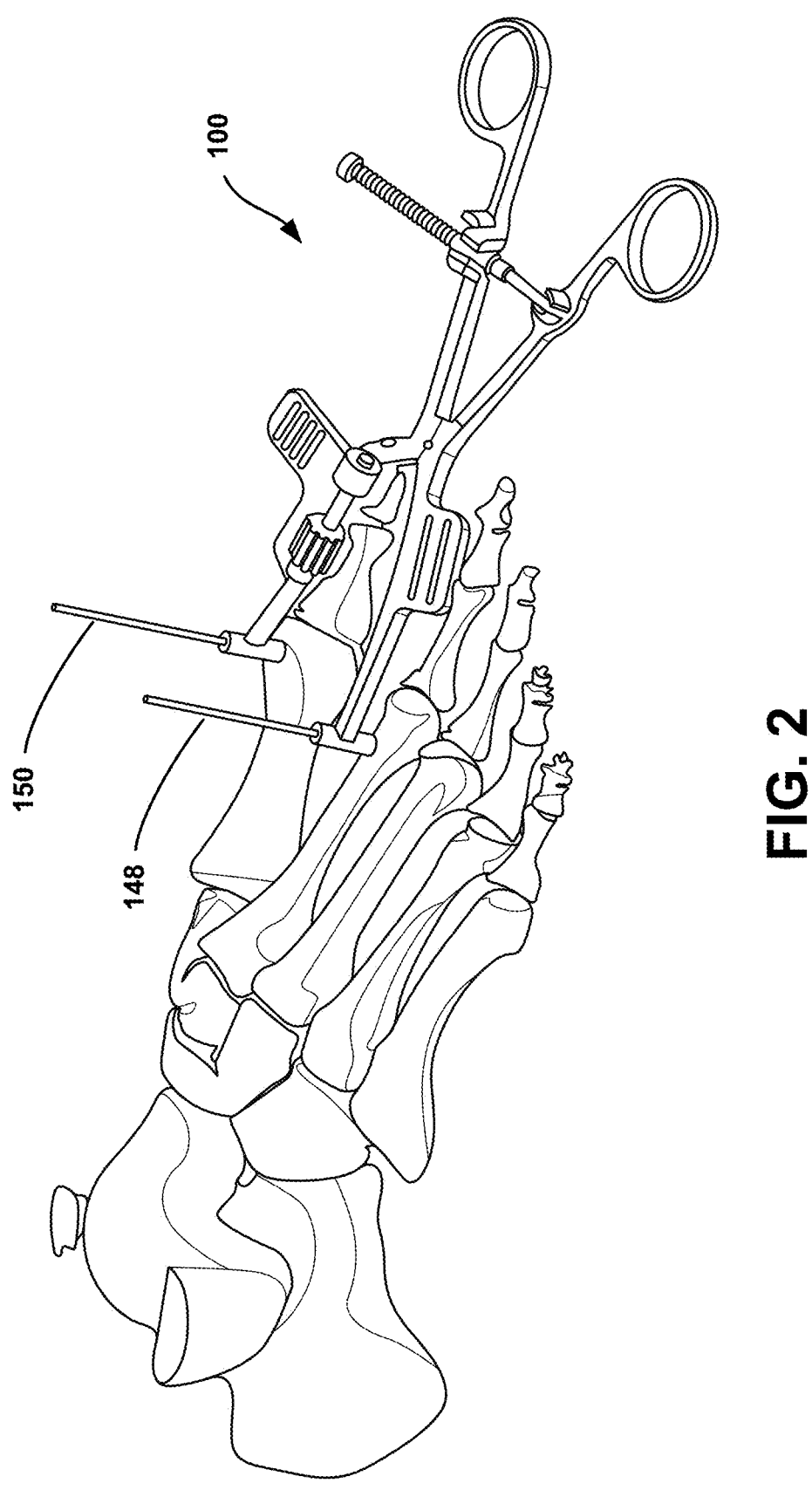
FIG. 2 is a perspective view of the example device of FIG. 1 with K-wires positioned in first metatarsal and second metatarsal.

As an initial step, a surgeon may free up the first metatarsal joint by resecting collateral ligaments. This will allow the first metatarsal joint to rotate and swing freely. Next, the surgeon will pin the device 100 to the patient using two K-wires. In one example, 1.6 mm K-wires are used. Preferred placement of these two K-wires is in the neck of the second metatarsal and dorsal medial in the neck of the first metatarsal, as shown in FIG. 2.

In one example, the surgeon may free hand the first K-wire 148 in the neck of the second metatarsal and then slide the first through-hole 124 of the first rod 102 of the device 100 over the inserted K-wire. Using the second through-hole 126 of the second rod 108 as a guide, the surgeon may then advance a second K-wire 150 into the neck of the first metatarsal in a dorsal-medial position.

In another example, the surgeon may free hand the first K-wire 148 in the first metatarsal in a dorsal-medial position and then slide the second through-hole 126 of the second rod 108 of the device 100 over the inserted K-wire. Using the first through-hole 124 of the first rod 102 as a guide, the surgeon may then advance a second K-wire 150 into the neck of the second metatarsal.

Next, with the first locking mechanism 114 in an unlocked position, the surgeon may adjust the distance between the first end 104 of the first rod 102 and the first end 110 of the second rod 108. Adjusting this distance adjusts the intermetatarsal angle. Once the desired adjustment to the intermetatarsal angle is achieved, the first locking mechanism 114 is moved to a locked position to thereby fix the distance between the first end 104 of the first rod 102 and the first end 110 of the second rod 108. Next, with the second locking mechanism 122 in an unlocked position, the surgeon may rotate the first portion 118 of the second rod 108 with respect to the second portion 120 of the second rod 108 to thereby adjust a pronation of the first metatarsal joint. Once the desired adjustment to the pronation of the first metatarsal joint is achieved, the second locking mechanism 122 is moved to a locked position to thereby fix the rotation of the first portion 118 of the second rod 108 with respect to the second portion 120 of the second rod 108.

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location, or other structural elements described as independent structures may be combined.

While various aspects and examples have been disclosed herein, other aspects and examples will be apparent to those skilled in the art. The various aspects and examples disclosed herein are for purposes of illustration and are not intended to be limiting, with the true scope being indicated by the following claims, along with the full scope of equivalents to which such claims are entitled. It is also to be understood that the terminology used herein is for the purpose of describing particular examples only, and is not intended to be limiting.

Example methods and systems are described herein. It should be understood that the words "example," "exemplary," and "illustrative" are used herein to mean "serving as an example, instance, or illustration." Any example or feature described herein as being an "example," being "exemplary," or being "illustrative" is not necessarily to be construed as preferred or advantageous over other examples or features. The examples described herein are not meant to be limiting. It will be readily understood that the aspects of the present disclosure, as generally described herein, and illustrated in the figures, can be arranged, substituted, combined, separated, and designed in a wide variety of different
configurations, all of which are explicitly contemplated
herein.

Furthermore, the particular arrangements shown in the
Figures should not be viewed as limiting. It should be
understood that other examples may include more or less of
each element shown in a given Figure. Further, some of the
illustrated elements may be combined or omitted. Yet fur-
ther, an example may include elements that are not illus-
trated in the Figures.

In the following description, numerous specific details are
set forth to provide a thorough understanding of the dis-
closed concepts, which may be practiced without some or all
of these particulars. In other instances, details of known
devices and/or processes have been omitted to avoid unnecessarily obscuring the disclosure. While some concepts will
be described in conjunction with specific examples, it will be
understood that these examples are not intended to be
limiting.

As used herein, "coupled" means associated directly as
well as indirectly. For example, a member A may be directly
associated with a member B, or may be indirectly associated
therewith, e.g., via another member C. It will be understood
that not all relationships among the various disclosed ele-
ments are necessarily represented.

Unless otherwise indicated, the terms "first," "second,"
etc. are used herein merely as labels, and are not intended to
impose ordinal, positional, or hierarchical requirements on
the items to which these terms refer. Moreover, reference to,
e.g., a "second" item does not require or preclude the existence of, e.g., a "first" or lower-numbered item, and/or,
e.g., a "third" or higher-numbered item.

Reference herein to "one embodiment" or "one example"
or "an example" means that one or more feature, structure,
or characteristic described in connection with the example is
included in at least one implementation. The phrases "one
embodiment" or "one example" or "an example" in various
places in the specification may or may not be referring to the
same example.

As used herein, a system, apparatus, structure, article,
element, component, or hardware "configured to" perform a
specified function is indeed capable of performing the
specified function without any alteration, rather than merely
having potential to perform the specified function after
further modification. In other words, the system, apparatus,
structure, article, element, component, or hardware "config-
ured to" perform a specified function is specifically selected,
created, implemented, utilized, programmed, and/or
designed for the purpose of performing the specified func-
tion. As used herein, "configured to" denotes existing characteristics of a system, apparatus, structure, article, element,
component, or hardware which enable the system, appara-
tus, structure, article, element, component, or hardware to
perform the specified function without further modification.
For purposes of this disclosure, a system, apparatus, structure, article, element, component, or hardware described as
being "configured to" perform a particular function may
additionally or alternatively be described as being "adapted
to" and/or as being "operative to" perform that function.

The limitations of the following claims are not written in
means-plus-function format and are not intended to be
interpreted based on 35 U.S.C. § 112(f), unless and until
such claim limitations expressly use the phrase "means for"
followed by a statement of function void of further structure.

By the term "about," "approximately," or "substantially"
with reference to amounts or measurement values described
herein, it is meant that the recited characteristic, parameter, or value need not be achieved exactly, but that deviations or
variations, including for example, tolerances, measurement
error, measurement accuracy limitations and other factors
known to those of skill in the art, may occur in amounts that
do not preclude the effect the characteristic was intended to
provide. For example, in one embodiment, the term "about"
can refer to ±5% of a given value.

Illustrative, non-exhaustive examples, which may or may
not be claimed, of the subject matter according the present
disclosure are provided below.

What is claimed is:

1. A device comprising:
a first rod having a first end and a second end opposite the
first end;
a second rod having a first end and a second end opposite
the first end, wherein the first rod is rotatably coupled
to the second rod between the first end of the second
rod and the second end of the second rod, and wherein
a movement of the second end of the first rod towards
the second end of the second rod causes a distance
between the first end of the first rod and the first end of
the second rod to increase;
a first locking mechanism comprising a locking rod
configured to pivot relative to one of the first and
second rods between an open position and a closed
position, wherein, in the open position, the locking rod
is coupled to one of the first and second rods, and
wherein in the closed position, the locking rod is
coupled to both of the first and second rods, wherein
when the locking rod is in the closed position, the
locking mechanism is configured to fix the distance
between the first end of the first rod and the first end of
the second rod;
a joint positioned between a first portion of the second rod
including the first end and a second portion of the
second rod including the second end, wherein the joint
enables a rotation of the first portion of the second rod
with respect to the second portion of the second rod
about a longitudinal axis of the first portion of the
second rod;
a handle coupled to the first portion of the second rod; and
a second locking mechanism configured to fix the rotation
of the first portion of the second rod with respect to the
second portion of the second rod, wherein the second
locking mechanism comprises a knob configured to
rotate about the longitudinal axis of the first portion of
the second rod between a first position in which the first
portion of the second rod is freely rotatable with respect
to the second portion of the second rod, and a second
position in which the first portion of the second rod is
rotatably fixed with respect to the second portion of the
second rod.

2. The device of claim 1, wherein the first end of the first
rod includes a first through-hole configured to receive a first
K-wire, and wherein the first end of the second rod includes
a second through-hole configured to receive a second
K-wire.

3. The device of claim 2, wherein the first through-hole
and the second through-hole each include a gripping mecha-
nism configured to prevent the first K-wire and the second
K-wire from slipping.

4. The device of claim 1,
wherein a rotation of the handle corresponds to the
rotation of the first portion of the second rod with
respect to the second portion of the second rod about
the longitudinal axis of the first portion of the second
rod.

5. The device of claim 4, wherein the handle comprises a tab with a plurality of ridges.

6. The device of claim 1, wherein the locking rod comprises a threaded rod, wherein a rotation of a knob positioned on the threaded rod in a clock-wise direction causes the distance between the first end of the first rod and the first end of the second rod to decrease.

7. The device of claim 6, wherein the threaded rod is positioned adjacent the second end of the first rod and the second end of the second rod.

8. The device of claim 1, wherein the knob includes a plurality of grooves, wherein, in the first position, a protrusion of the handle does not contact the plurality of grooves, and wherein, in the second position, the protrusion of the handle contacts one of the plurality of grooves such that the first portion of the second rod is rotatably fixed with respect to the second portion of the second rod.

9. The device of claim 1, wherein the second end of the first rod includes a first through-hole configured to receive a finger of a surgeon, and wherein the second end of the second rod includes a second through-hole configured to receive a second finger of the surgeon.

10. The device of claim 1, wherein the first rod is rotatably coupled to the second rod via a pin.

11. The device of claim 1, wherein the first rod and the second rod are configured to move with respect to one another in a plane.

* * * * *